(12) United States Patent
Elemans et al.

(10) Patent No.: US 10,117,449 B2
(45) Date of Patent: Nov. 6, 2018

(54) EXTRUSION PROCESS

(71) Applicant: DSM IP ASSETS B.V., Heerlen (NL)

(72) Inventors: Petrus Henricus Maria Elemans, Basel (CH); Adrian Willem Meesen, Basel (CH); Alexandra Teleki, Basel (CH); Bruno Leuenberger, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 641 days.

(21) Appl. No.: 14/381,743

(22) PCT Filed: Feb. 27, 2013

(86) PCT No.: PCT/EP2013/053843
§ 371 (c)(1),
(2) Date: Aug. 28, 2014

(87) PCT Pub. No.: WO2013/127807
PCT Pub. Date: Sep. 6, 2013

(65) Prior Publication Data
US 2015/0056345 A1 Feb. 26, 2015

(30) Foreign Application Priority Data
Feb. 28, 2012 (EP) ..................... 12157279

(51) Int. Cl.
| | | |
|---|---|---|
| A23C 9/12 | (2006.01) | |
| A23L 1/275 | (2006.01) | |
| A23K 40/25 | (2016.01) | |
| A61K 8/31 | (2006.01) | |
| A61Q 19/00 | (2006.01) | |
| A23D 7/005 | (2006.01) | |
| A23D 7/04 | (2006.01) | |
| A23K 40/20 | (2016.01) | |
| A23K 20/174 | (2016.01) | |
| A23K 20/179 | (2016.01) | |
| A23K 20/147 | (2016.01) | |
| A23K 20/158 | (2016.01) | |
| A23K 20/163 | (2016.01) | |
| A23K 20/10 | (2016.01) | |
| A23P 30/20 | (2016.01) | |
| A23L 29/212 | (2016.01) | |
| A23L 27/00 | (2016.01) | |
| A23L 5/44 | (2016.01) | |
| A23L 33/15 | (2016.01) | |
| A23C 9/14 | (2006.01) | |
| A23C 9/18 | (2006.01) | |

(52) U.S. Cl.
CPC .......... *A23L 1/2753* (2013.01); *A23D 7/0053* (2013.01); *A23D 7/04* (2013.01); *A23K 20/10* (2016.05); *A23K 20/147* (2016.05); *A23K 20/158* (2016.05); *A23K 20/163* (2016.05); *A23K 20/174* (2016.05); *A23K 20/179* (2016.05); *A23K 40/20* (2016.05); *A23K 40/25* (2016.05); *A23L 5/44* (2016.08); *A23L 27/70* (2016.08); *A23L 29/212* (2016.08); *A23L 33/15* (2016.08); *A23P 30/20* (2016.08); *A61K 8/31* (2013.01); *A61Q 19/00* (2013.01); *A23V 2002/00* (2013.01)

(58) Field of Classification Search
CPC ............................ A23L 1/2753; A23K 20/147
See application file for complete search history.

(56) References Cited

U.S. PATENT DOCUMENTS

2002/0044968 A1* 4/2002 van Lengerich ......... B01J 13/02
424/469

FOREIGN PATENT DOCUMENTS

| CN | 101291598 | 10/2008 |
|---|---|---|
| EP | 1 097 694 | 5/2001 |
| EP | 1 116 515 | 7/2001 |
| WO | WO 2010/040683 | 4/2010 |

OTHER PUBLICATIONS

Wang et al., "Modified Polymers", 2$^{nd}$ Ed., Higher Education Textbooks, Polymer Science and Engineering Textbook Series, China Light Industries Press (May 2008), 4 pages.
International Search Report for PCT/EP2013/053843, dated Jun. 10, 2013.
McClements et al., "Structured emulsion-based delivery systems: Controlling the digestion and release of lipophilic food components", *Advances in Colloid and Interface Science*, vol. 159, No. 2, Sep. 15, 2010, pp. 213-228.

\* cited by examiner

*Primary Examiner* — D Lawrence Tarazano
*Assistant Examiner* — Philip Dubois
(74) *Attorney, Agent, or Firm* — Nixon & Vanderhye P.C.

(57) ABSTRACT

The present invention relates to a process for the production of extruded formulations (=extrudates) comprising dispersion droplets, to such formulations as well as to the use of such formulations in food, feed, personal care applications.

17 Claims, No Drawings

EXTRUSION PROCESS

This application is the U.S. national phase of International Application No. PCT/EP2013/053843 filed 27 Feb. 2013 which designated the U.S. and claims priority to EP Patent Application No. 12157279.6 filed 28 Feb. 2012, the entire contents of each of which are hereby incorporated by reference.

The present invention relates to a process for the production of extruded formulations (=extrudates) comprising dispersion droplets, to such formulations as well as to the use of such formulations in food, feed, personal care applications.

More precisely, the present invention relates to a process for the production of extruded formulations comprising dispersion droplets, wherein the dispersion comprises at least one carotenoid, at least one emulsifying protective colloid and water.

The terms "emulsion" and "dispersion" in the context of the present invention are synonyms. A dispersion in the context of the present invention comprises (at least). one (or more) carotenoid and one (or more) emulsifying protective colloid and water.

There are many ways to formulate carotenoids. The types of formulations are depending i.e. on the use of these formulations in the final application as well as on the kind of material (ingredients) which are used. However, the most important and demanding formulations are the so-called dried dispersions. The carotenoid is emulsified into an aqueous phase containing a matrix material and/or a suitable emulsifying protective colloid. After drying, the carotenoid is embedded in the matrix material. It is possible that the carotenoid is (partially) crystallised in the extrudate.

Known technologies for dispersion are e.g. rotor-stator-systems, high pressure homogenizers or ultrasonic devices. A major disadvantage of these technologies is that a relatively low viscosity (usually below 1 Pas) is required, leading to high amounts of water in the dispersion. Usually these processes require the use of an organic solvent which has to be removed after dispersion or precipitation.

Extrusion processes (and extruders) are well known in the field of formulations. They can be used for many different kinds of materials, such as thermoplastics and rubbers, as well as food- and feedstuffs.

The main advantages of using the extrusion technology is that high viscous solutions can be formulated and less water can be used for the dispersion, which then requires less drying. Furthermore an extrusion process can be run as a continuous process and it can be run without organic solvents.

It can be found in the prior art that emulsions comprising fat soluble vitamins are extruded. US 2004/0201116 discloses pellets which are obtained by a combination of producing emulsions using devices like high pressure homogenizers with subsequent direct pelleting or extrusion as a second process step.

The goal of the present invention was to find a way for the production of extrudates comprising dispersion droplets, which comprise carotenoid(s).

Carotenoids are distinctly different from lipophilic vitamins and lipophilic flavours. These lipophilic vitamins are either liquid or can easily be made liquid by using reasonable temperatures well below 100° C. Carotenoids are lipophilic, cannot be melted around 100° C., and decompose at higher temperatures. They are classical representative of the so-called sparingly soluble lipophilic actives.

A new way for the production of such extrudates was found. Surprisingly it was found out that when the dispersion process is carried out inside the extruder, the process as well as the obtained extrudates are improved.

When the dispersion process is carried out in the extruder (extrudation apparatus), this results in extrudates, wherein
(i) very small average dispersion droplets sizes can be obtained, and
(ii) a very narrow and monomodal distribution of the droplet sizes is obtained, and
(iii) such a process can easily be run as a continuous process, and
(iv) no organic solvent is used and
(v) less water can be used and therefore less energy for drying the extrudate is necessary.

Therefore the present invention relates to a process of production of an extrudate, wherein that extrudate comprises dispersion droplets, wherein these dispersion droplets comprise at least one carotenoid and at least one emulsifying protective colloid and water, characterised in that the emulsifying process is carried out in the extruder.

The term "carotenoid" as used herein comprises a natural or synthetic carotene or structurally related polyene compound which can be used as a functional health ingredient or colorant for food, such as α- or β-carotene, 8'-apo-β-carotenal, 8'-apo-β-carotenoic acid esters such as the ethyl ester, canthaxanthin, astaxanthin, lycopene, lutein, zeaxanthin or crocetin, or mixtures thereof. The preferred carotenoids are β-carotene, lycopene and lutein and mixtures thereof, especially β-carotene.

Therefore a preferred embodiment of the present invention is a process as described above, wherein the one or more carotenoid is chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin.

In an especially preferred process the carotenoid is β-carotene.

At least one emulsifying protective colloid is used in the process according to the present invention. The term emulsifying protective colloid covers all protective colloids having emulsifying properties. Any commonly known and used emulsifying protective colloid can be used. The emulsifying protective colloid can be chosen depending on the final use of the extrudate afterwards. That means if the extrudate obtained by the process according to the present invention is used in food or feed products, the emulsifying protective colloid must be food or feed grade.

Suitable emulsifying protective colloids are i.e. modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), xanthan gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

The starches can be modified physically and chemically. Pregelatinized starches are examples of physically modified starches. Acidic modified, oxidized, cross-linked, starch esters, starch ethers and cationic starches are examples of chemically modified starches.

A preferred embodiment therefore relates to a process, wherein at least one emulsifying protective colloid is chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), xanthan gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof).

Water is also used in the process according to the present invention.

It is also possible to add further ingredients (auxiliary agents) during the process of formulation (extrudation). Such auxiliary agents can be useful for the extrusion process and/or for the extrudate and/or for the product (or application), wherein the extrudate is used afterwards.

Such auxiliary agents are for example antioxidants (such as ascorbic acid or salts thereof, tocopherols (synthetic or natural); butylated hydroxytoluene (BHT); butylated hydroxyanisole (BHA); propyl gallate; tert. butyl hydroxyquinoline and/or ascorbic acid esters of a fatty acid); ethoxyquin, plasticisers, stabilisers, humectants (such as glycerine, sorbitol, polyethylene glycol) protective colloids without emulsifying properties, gelling agents (such as chitosan), dyes, fragrances, fillers (such as maltodextrin) and buffers.

These auxiliary agents are added optionally. When added then the amount of the auxiliary agents goes from 0.1 to 50 weight-% (wt-%), based on the total weight of the extrudate.

The extrudates obtained by the process according to the present invention comprise:
  0.5 wt-%-50 wt-%, based on the total weight of the extrudate, of at least one carotenoid, and
  5 wt-%-80 wt-%, based on the total weight of the extrudate, of at least one emulsifying protective colloid, and
  1 wt-%-90 wt-%, based on the total weight of the extrudate, of water, and optionally
  0.1 wt-%-50 wt-%, based on the total weight of the extrudate, of at least one auxiliary agent.

All the percentages always add up to 100.

All the preferences listed above for the carotenoids, the emulsifying protective colloids and the auxiliary agents also apply to the composition of the extrudate.

Preferably 1 wt-%-45 wt-%, based on the total weight of the extrudate, of at least one carotenoid is used. More preferably 1 wt-%-30 wt-%, especially preferred 1 wt-%-20 wt-%, most preferred 1 wt-%-15 wt-%, based on the total weight of the extrudate, of at least one carotenoid is used.

Preferably 15 wt-%-80 wt-%, more preferably 30 wt-%-80 wt-%, most preferably 50 wt-%-80 wt-%, based on the total weight of the extrudate, of at least one emulsifying protective colloid is used.

Preferably 1 wt-%-80 wt-%, more preferably 1 wt-%-60 wt-%, based on the total weight of the extrudate, of water is used. As already mentioned above, it also possible to use a low amount of water. Therefore 5 wt-%-30 wt-%, based on the total weight of the extrudate, of water can be used. Such a low amount of water cannot be used when an extrudate is produced by adding the dispersion into the extruder.

For the modified food starches the water content is preferably 10 wt-%-30 wt-%, based on the total weight of the extrudate.

One of the advantages of the present invention is that the size distribution of the average droplet sizes of the dispersion inside the extrudate is narrow and monomodal. This means that the carotenoid is nearly homogenously distributed inside the extrudate, which allows afterwards very precise dosages.

It is also possible (but not essential) that the dispersion can be filtered before the extrusion process.

Furthermore, the process according to the present invention allows to producing very small sized droplets inside the extrudate. The average droplet size can be as small as 50 nm. Usually the droplets are smaller than 1 μm.

Preferably the average droplet ($d_{3,2}$) is between 50 nm and 1000 nm.

The droplet sizes are measured by using commonly known and standardized methods. Suitable methods are light scattering or laser diffraction. The given values of the droplet sizes are always ($d_{3,2}$).

More preferably the average droplet ($d_{3,2}$) is between 50 nm and 500 nm, especially preferred 100-300 nm.

The extrusion process is characterised in that the dispersion is carried out inside the extruder. Usually the three main ingredients (carotenoid and emulsifying protective colloid and water) are added at different inlets of the extruder process. These inlets are arranged separated from each other. When (optionally) auxiliary agents are added, they can be added together with one or more of the main ingredients or they can also be added in a separate step.

Usually the emulsifying protective colloid is added first, then the water and then the carotenoid is added. It is also possible that one ingredient is added through more than one inlet of the extruder at different locations. Therefore a further embodiment of the present invention relates to a process, wherein the emulsifying protective colloid (or a mixture of emulsifying protective colloids) is added first, then the water and then afterwards the carotenoid (or a mixture of carotenoids).

A preferred embodiment of the present invention relates to a process wherein the carotenoid is β-carotene. In this case β-carotene is either added
  (i) as a liquid (molten) into the extruder, or
  (ii) as a solid powder (optionally premixed with at least one modified (food) starch and wherein the powder can be added to the process at the start of the extruder or at any stage).

The temperature inside the extruder is usually between 20 and 220° C. Preferably the temperature of extrudate exiting the extruder is <100° C. The total residence time for the ingredients in the extruder is usually between 1 and 400 s.

The amount of shear of the extrudation process according to the present invention is usually 100 to 200000 units.

Furthermore, it is also possible to pump inert gas through the extruder. The inert gas is usually pumped in at the entrance of the extruder. But it could also be pumped in at any stage of the extrusion process (also through several inlets at different locations). Inert gas can be helpful to protect sensible ingredients.

The extruder comprises usually one or more screw shafts on which various conveying or kneading type screw elements are mounted.

The material is transported by these elements through the extruder (optionally under pressure and elevated temperature). At the end (exit) of the extruder there can be a die through which the extruded material is pressed. Afterwards the extruded material is dried and cut (or also vice versa). The extruder can have several inlets through which the material can be added.

In the case of the present invention there are several inlets to add the emulsifying protective colloid(s), the carotenoid(s), water and optionally the auxiliary agents.

A further embodiment of the present invention relates to new extrudates. These inventive extrudates comprise dispersion droplets which have a very small average droplet size, and wherein the distribution of the droplet sizes is narrow and monomodal.

Therefore a further embodiment of the present invention relates to extrudates comprising dispersion droplets, wherein these dispersion droplets comprise
- at least one carotenoid and
- at least one emulsifying protective colloid, and
- water, and optionally
- at least one auxiliary agent.

A preferred embodiment of the present invention relates to extrudates comprising dispersion droplets, wherein these dispersion droplets comprise
- at least one carotenoid and
- at least one emulsifying protective colloid, and
- water, and optionally
- at least one auxiliary agent,
- characterised in that the average particle size of the dispersion droplets are less than 1000 nm (preferably the average particle size of the dispersion droplets is between 50 nm and 500 nm, more preferably 100 nm-300 nm).

The average particle size of the dispersion droplets are measured by laser diffraction with a Malvern Mastersizer 2000 and Hydro 2000 S sample dispersion unit. The average particle size of the dispersion droplets can also be determined by dynamic light scattering, e.g. with a Malvern Zetasizer Nano.

It is possible that in the extrudate some of the carotenoid is crystallised (precipitated), due to the solubility of the carotenoids in oil.

Preferred extrudates according to the present invention comprise:
- 0.5 wt-%-50 wt-%, based on the total weight of the extrudate, of at least one carotenoid, and
- 5 wt-%-90 wt-%, based on the total weight of the extrudate, of at least one emulsifying protective colloid, and
- 1 wt-%-80 wt-%, based on the total weight of the extrudate, of water and optionally
- 0.1 wt-%-50 wt-%, based on the total weight of the extrudate, of at least one auxiliary agent,
- characterised in that the average particle size of the dispersion droplets are less than 1000 nm (preferably the average particle size of the dispersion droplets is between 50 nm and 500 nm, more preferably 100 nm-300 nm).

More preferred are extrudates comprising
- 1 wt-%-30 wt-%, based on the total weight of the extrudate, of at least one carotenoid chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin (most preferred is β-carotene), and
- 15 wt-%-80 wt-%, based on the total weight of the extrudate, of at least one emulsifying protective colloid, wherein the emulsifying protective colloid is chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia, xanthan gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and
- 1 wt-%-60 wt-%, based on the total weight of the extrudate, of water, and optionally
- 0.1 wt-%-50 wt-%, based on the total weight of the extrudate, of at least one auxiliary agent, wherein the auxiliary agent is chosen from the group consisting of antioxidants (such as ascorbic acid or salts thereof, tocopherol (synthetic or natural); butylated hydroxytoluene (BHT); butylated hydroxyanisole (BHA); propyl gallate; tert. butyl hydroxyquinoline and/or ascorbic acid esters of a fatty acid); ethoxyquin, plasticisers, stabilisers, humectants (such as glycerine, sorbitol, polyethylene glycol) protective colloids without emulsifying properties, gelling agents (such as chitosan), dyes, fragrances, fillers (such as maltodextrin) and buffers.
- characterised in that the average particle size of the dispersion droplets are less than 1000 nm (preferably the average particle size of the dispersion droplets is between 50 nm and 500 nm, more preferably 100 nm-300 nm).

Also more preferred are extrudates comprising
- 1 wt-%-20 wt-%, based on the total weight of the extrudate, of at least one carotenoid chosen from the group consisting of α-carotene, β-carotene, 8'-apo-β-carotenal, 8'-apo-β-carotenoic acid esters such as the ethyl ester, canthaxanthin, astaxanthin, lycopene, lutein, zeaxanthin and crocetin (most preferred is β-carotene), and
- 15 wt-%-80 wt-%, based on the total weight of the extrudate, of at least one emulsifying protective colloid, wherein the emulsifying protective colloid is chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia, xanthan gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, PG ester and sugar ester (as well as derivatives thereof), and
- 5 wt-%-30 wt-%, based on the total weight of the extrudate, of water, and optionally 0.1 wt-%-50 wt-%, based on the total weight of the extrudate, of at least one auxiliary agent, wherein the auxiliary agent is chosen from the group consisting of antioxidants (such as ascorbic acid or salts thereof, tocopherol (synthetic or natural); butylated hydroxytoluene (BHT); butylated hydroxyanisole (BHA); propyl gallate; tert. butyl hydroxyquinoline and/or ascorbic acid esters of a fatty acid); ethoxyquin, plasticisers, stabilisers, humectants (such as glycerine, sorbitol, polyethylene glycol) protective colloids, dyes, fragrances, fillers (such as maltodextrin), protective and buffers, characterised in that the average particle size of the dispersion droplets is less than 500 nm (preferably the average particle size of the dispersion droplets is between 50 nm and 300 nm).

Especially preferred are extrudates comprising 1 wt-%-20 wt-%, based on the total weight of the extrudate, of β-carotene, and 50 wt-%-80 wt-%, based on the total weight of the extrudate, of modified (food) starches, and 10 wt-%-30 wt-%, based on the total weight of the extrudate, of water, and optionally 0.1 wt-%-50 wt-%, based on the total weight of the extrudate, of at least one auxiliary agent, wherein the auxiliary agent is chosen from the group consisting of antioxidants (such as ascorbic acid or salts thereof, tocopherol (synthetic or natural); butylated hydroxytoluene (BHT); butylated hydroxyanisole (BHA); propyl gallate; tert. butyl hydroxyquinoline and/or ascorbic acid esters of a fatty acid); ethoxyquin, plasticisers, stabilisers, humectants (such as glycerine, sorbitol, polyethylene glycol) protective colloids, dyes, fragrances, fillers and buffers, characterised in that the average particle size of the dispersion droplets is less than 500 nm (preferably the average particle size of the dispersion droplets is between 50 nm and 300 nm).

The extrudates as obtained by the process as described above can be used in many fields of applications. Preferably the extrudates as disclosed and described above are used in food, feed and personal care products.

Therefore a further embodiment of the present invention relates to the use of the extrudates as disclosed and described above in food, feed and/or personal care products. It is to be mentioned that dietary supplements are part of our definition of food products.

A further embodiment of the present invention relates to food, feed or personal care products comprising at least one of the extrudates as disclosed and described above.

The following Examples serve to illustrate the invention. All percentages and parts (if not otherwise indicated) are related to the weight. The temperature is given (if not otherwise indicated) in degree Celsius.

EXAMPLES

Example 1: Dispersion of β-Carotene in Modified Food Starch

The extrusion dispersion of β-carotene in 10.5 g modified food starch was conducted on a laboratory-scale conical twin-screw (batch) extruder (DSM Xplore 15 ml microcompounder). 10.5 g of modified food starch (HICAP 100, National Starch), was mixed with 0.75 g of β-carotene (DSM Nutritional Products) and 3.75 g demineralized water. The extruder was operated at a screw speed of 120 rpm and a barrel temperature of 200° C. The feed hopper and extruder were purged with nitrogen. The mixture was placed in the feed hopper and allowed to pass once through the extruder.

The obtained extrudate was partly soluble in water resulting in an orange, cloudy solution stable over 12 hours. This solution was filtered either with a folded filter paper (grade 597½: 5-7 μm) or a syringe driven filter unit (0.22 μm). Filtration with the larger pores resulted in a turbid, light-yellow solution, while the solution from the fine filter was clear. The hydrodynamic droplet size in these solutions was measured by dynamic light scattering (Malvern Zetasizer). The average droplet size (Z-Average) in the clear solution was 184 nm, while the turbid solution also contained some larger droplets/particles resulting in a Z-Average of 625 nm.

The invention claimed is:

1. A process for production of an extrudate which comprises dispersion droplets, wherein the process comprises:
   (i) introducing emulsion ingredients consisting of at least one carotenoid, modified food starch as an emulsifying protective colloid for the carotenoid, and water into at least one feed hopper of a nitrogen gas purged extruder having an extruder barrel and an extruder screw,
   (ii) operating the extruder so as to emulsify the emulsion ingredients in the extruder barrel to thereby form an emulsified dispersion of dispersion droplets having an average droplet size ($d_{3,2}$) between 50 nm and 1000 nm consisting of the carotenoid dispersed within the modified food starch as an emulsifying protective colloid for the carotenoid, and
   (ii) extruding the emulsified dispersion consisting of the dispersion droplets dispersed within the modified food starch from the extruder barrel to form an extrudate which consists of the dispersion droplets dispersed within the modified food starch.

2. The process according to claim 1, wherein the process is carried out in the absence of an organic solvent.

3. The process according to claim 1, wherein the carotenoid is at least one selected from the group consisting of α-carotene, β-carotene, 8'-apo-β-carotenal, 8'-apo-β-carotenoic acid esters, canthaxanthin, astaxanthin, lycopene, lutein, zeaxanthin and crocetin.

4. The process according to claim 1, wherein the carotenoid is β-carotene.

5. The process according to claim 1, wherein the at least one carotenoid is present in step (i) in an amount of 0.5 wt-% 50 wt-%, based on the total weight of the extrudate.

6. The process according to claim 1, wherein the modified food starch is present in step (i) in an amount of 5 wt-% 80 wt-%, based on the total weight of the extrudate.

7. The process according to claim 1, wherein the water is present in step (i) in an amount of 1 wt-%-90 wt-%, based on the total weight of the extrudate.

8. The process according to claim 7, wherein the water is present in an amount of 5 wt-%-30 wt-%, based on the total weight of the extrudate.

9. The process according to claim 1, wherein the emulsion ingredients of step (i) further consist of 0.1 wt-%-50 wt-%, based on the total weight of the extrudate, of at least one auxiliary agent.

10. The process according to claim 9, wherein the auxiliary agent is at least one selected from the group consisting of antioxidants, ethoxyquin, plasticisers, stabilisers, humectants, protective colloids without emulsifying properties, gelling agents, dyes, fragrances, fillers and buffers.

11. The process according to claim 1, wherein the step (i) comprises sequentially adding to the extruder (1) the modified food starch as an emulsifying protective colloid for the at least one carotenoid, (2) the water and thereafter (3) the at least one carotenoid.

12. The process according to claim 1, wherein the carotenoid is β-carotene, and wherein step (i) comprises adding the β-carotene in a molten form to the extruder in advance of the at least one emulsifying protective colloid and the water.

13. The process according to claim 1, wherein the carotenoid is β-carotene, and wherein step (i) comprises adding the β-carotene to the extruder as a powder.

14. The process according to claim 1, wherein the temperature inside the extruder is between 20° C. and 220° C.

15. The process according to claim 1, wherein the total residence time for the ingredients is between 1 and 400 s.

16. The process according to claim 13, wherein step (i) comprises adding the β-carotene to the extruder in a mixture with the modified food starch.

17. A food, feed or personal care product which comprises an extrudate obtained by the process of claim 1.

* * * * *